United States Patent [19]

Brunner et al.

[11] 4,380,640
[45] Apr. 19, 1983

[54] NOVEL BENZTHIAZOLYLUREA DERIVATIVES, COMPOSITIONS CONTAINING THEM AND THEIR USE AS HERBICIDES

[75] Inventors: Hans-Georg Brunner, Lausen; Werner Föry, Basel, both of Switzerland

[73] Assignee: Ciba-Geigy Corporation, Ardsley, N.Y.

[21] Appl. No.: 224,583

[22] Filed: Jan. 12, 1981

[30] Foreign Application Priority Data

Jan. 21, 1980 [CH] Switzerland ............................ 464/80

[51] Int. Cl.³ .................... C07D 277/82; C07D 417/12
[52] U.S. Cl. ..................................... 548/163; 546/198; 71/88; 71/94; 71/95; 71/90
[58] Field of Search ....................... 548/163, 161, 164; 546/198

[56] References Cited

U.S. PATENT DOCUMENTS

| 3,503,990 | 3/1970 | Schoeu et al. | 260/326.15 |
| 3,682,945 | 8/1972 | Englehart | 548/163 |

FOREIGN PATENT DOCUMENTS

| 1932699 | 1/1970 | Fed. Rep. of Germany | 548/163 |
| 2284283 | 9/1974 | France | 548/163 |

OTHER PUBLICATIONS

Fleser et al., Agents Advanced Org. Chem., pp. 634 & 635, Reinhold, N.Y., N.Y., (1961).

*Primary Examiner*—Mary C. Lee
*Assistant Examiner*—W. B. Springer
*Attorney, Agent, or Firm*—Frederick H. Rabin

[57] ABSTRACT

The invention discloses novel herbicidally active and plant growth-regulating benzthiazolylurea derivatives of the formula

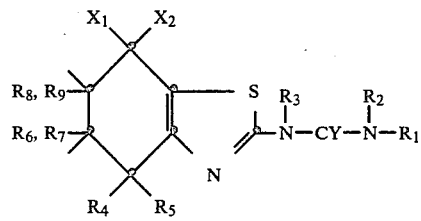

wherein $R_1$ is hydrogen, $C_1$–$C_6$alkyl, $C_3$–$C_6$alkenyl, $C_3$–$C_6$-alkylnyl or $C_3$–$C_6$cycloalkyl; $R_2$ has the same meaning as $R_1$ or is $C_1$–$C_6$alkoxy; $R_1$ and $R_2$, together with the nitrogen atom to which they are attached, also form a 5- to 6-membered heterocyclic ring which can be substituted by $C_1$–$C_3$alkyl; $R_3$ is hydrogen, $C_1$–$C_6$alkyl, an alkali metal cation or an alkaline earth metal cation or a $C_1$–$C_4$alkylammonium radical, the alkyl moieties of which can be substituted by OH, $NH_2$, CN or $C_1$–$C_4$alkoxy; $R_5$ to $R_9$ are preferably hydrogen or $C_1$–$C_4$alkyl, but can also have one of the other meanings defined more closely in the specification; $X_1$ and $X_2$, each independently of the other, is a $C_1$–$C_8$alkoxy or $C_1$–$C_8$alkylthio radical which can be substituted by halogen and/or interrupted by oxygen or sulfur, while $X_1$ and $X_2$ together can also be a double bonded oxygen atom or $C_2$–$C_3$alkylene-dioxide or -disulfide which can be substituted in the alkyl moiety by halogen, $C_1$–$C_6$alkyl or $C_1$–$C_6$alkoxy or $C_1$–$C_4$alkylthio; and Y is an oxygen or a sulfur atom.

10 Claims, No Drawings

NOVEL BENZTHIAZOLYLUREA DERIVATIVES, COMPOSITIONS CONTAINING THEM AND THEIR USE AS HERBICIDES

The present invention relates to novel benzthiazolylurea derivatives having herbicidal and plant growth-inhibiting properties. The invention also relates to the production of these compounds, to compositions containing them, and to methods of controlling unwanted plant growth, especially in crops of useful plants, which comprises the use thereof.

Benzthiazolylureas of similar structure are known from the literature (cf. for example German Offenlegungsschrift No. 1 932 699 and U.S. Pat. No. 3,682,945). The benzthiazolylurea derivatives of this invention are new and have excellent herbicidal properties.

The novel benzthiazolylurea derivatives have the formula

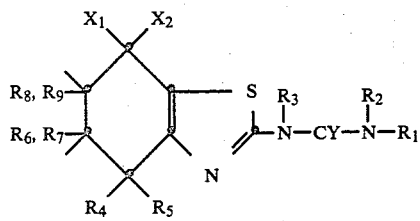

wherein
- $R_1$ is hydrogen, $C_1$–$C_6$alkyl, $C_3$–$C_6$alkenyl or $C_3$–$C_6$alkynyl or $C_3$–$C_6$cycloalkyl,
- $R_2$ has the same meaning as $R_1$ or is $C_1$–$C_4$alkoxy,
- $R_1$ and $R_2$, together with the nitrogen atom to which they are attached, also form a 5- to 6-membered heterocyclic ring which can be substituted by $C_1$–$C_3$alkyl,
- $R_3$ is hydrogen, $C_1$–$C_6$alkyl, $C_3$–$C_6$alkenyl or $C_3$–$C_6$alkynyl, or is a radical $(1/n) M^{n\oplus}$, wherein M is an n-valent alkali metal cation or alkaline earth metal cation or an ammonium radical

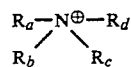

wherein each of
- $R_a$, $R_b$, $R_c$ and $R_d$ independently is hydrogen, benzyl or $C_1$–$C_4$alkyl which can be substituted by OH, $NH_2$, CN or $C_1$–$C_4$alkoxy,
- $R_4$ and $R_8$, each independently of the other, is hydrogen, halogen, or $C_1$–$C_8$alkyl which is unsubstituted or substituted by halogen or interrupted by oxygen or sulfur,
- $R_5$ and $R_9$, each independently of the other, has the same meaning as $R_4$, and is additionally cyano, phenyl which is unsubstituted or substituted by halogen, nitro, trifluoromethyl, $C_1$–$C_4$alkoxy or $C_1$–$C_4$alkylthio, or is the carboxyl group, a $C_1$–$C_4$alkoxycarbonyl or $C_1$–$C_4$alkylthiocarbonyl group, the $(1/n)M^{n\oplus}$ carboxyl salt, the carbamoyl group or a N-($C_1$–$C_8$alkyl)carbamoyl group, the alkyl moiety of which can be substituted by halogen and/or interrupted by oxygen or sulfur,
- $R_6$ and $R_7$, each independently of the other, is hydrogen, $C_1$–$C_8$alkyl which is unsubstituted or substituted by halogen or interrupted by oxygen or sulfur; phenyl which is unsubstituted or substituted by halogen, nitro, trifluoromethyl, $C_1$–$C_4$alkoxy or $C_1$–$C_4$alkylthio;
$C_3$–$C_8$cycloalkyl which is unsubstituted or substituted by halogen, $C_1$–$C_6$alkoxy or $C_1$–$C_4$alkylthio;
$C_3$–$C_8$alkenyl or $C_3$–$C_8$alkynyl, each of which is unsubstituted or substituted by halogen or interrupted by oxygen or sulfur;
whilst $R_6$ and $R_7$ together can form a $C_2$–$C_5$alkenylene chain which can be substituted by halogen, $C_1$–$C_6$alkyl or
$C_1$–$C_6$alkoxy or $C_1$–$C_4$alkylthio;
$R_4$ and $R_6$, and $R_6$ and $R_8$, together can form a $C_1$–$C_5$alkylene chain which can be substituted by halogen, $C_1$–$C_6$alkyl or $C_1$–$C_6$alkoxy or $C_1$–$C_4$alkylthio;
Y is an oxygen or a sulfur atom, and
$X_1$ and $X_2$, each independently of the other, is a $C_1$–$C_8$alkoxy or $C_1$–$C_8$alkylthio radical which can be substituted by halogen and interrupted by oxygen or sulfur, whilst $X_1$ and $X_2$ together are a double bonded oxygen atom, $C_2$–$C_4$alkylenedioxide or -disulfide which can be substituted in the alkyl moiety by halogen, $C_1$–$C_6$alkyl or $C_1$–$C_6$alkoxy, $C_1$–$C_4$alkylthio or halomethyl.

In the above definitions, the alkyl radicals or alkyl moieties of alkoxy or alkylthio radicals contain the indicated number of carbon atoms. However, they are preferably lower radicals which can be unbranched, such as methyl, ethyl, propyl and butyl, or branched, such as isopropyl, sec-butyl, isobutyl and tert-butyl. The preferred alkenyl and alkynyl radicals are allyl, methallyl, buten-2-yl, propargyl, methylpropargyl and butyn-2-yl. Preferred cycloalkyl radicals are cyclopropyl, cyclopentyl and cyclohexyl. Alkylene chains have preferably 3 to 5 chain members so as to form 5- and 6-membered rings with the carbon atoms to which they are attached. The heterocyclic rings formed by $R_1$ and $R_2$ also have 5 or 6 ring members and are preferably pyrole, pyrrolidine, pyridine, methylpyridine, piperidine or morpholine.

The novel compounds of the formula I have good herbicidal action against both grass weeds and broad-leafed weeds, while interesting selectively has been observed in crops of monocots such as maize and cereals, and also in crops of individual dicots, e.g. soybeans. The novel compounds can be employed both as post-emergence and preemergence herbicides. Rates of application from 0.1 to 5 kg per hectare are normally required.

A total herbicidal action is achieved if the rate of application is sufficiently high. Application can be both pre- and postemergence, and the rates of application can vary within wide limits, e.g. from 0.1 to 10 kg of active ingredient per hectare.

The compounds of formula I also have good growth-regulating action (growth inhibition). In particular, they inhibit plant growth. The following effects may be cited as examples of the useful application of the compounds of the invention:
the reduction of the vegetative growth of soybeans and similar leguminous plants, resulting in an increase in yield of these crops;
the inhibition of unwanted growth of suckers in tobacco plants whose leading shoots have been cut, thereby promoting the formation of larger and finer leaves;

the inhibition of the growth of grass and dicots such as fruit trees, ornamental trees, bushes and hedgerows, with the aim of reducing cutting work;

the inhibition of the vegetative growth of cereals, resulting in plants with shorter and sturdy stalks which are not so easily lodged by the action of wind and rain.

The compounds of the formula I can also be used for defoliating and desiccating parts of plants above the soil, wherever this is desired. Potato and cotton crops are treated in this manner, e.g. shortly before harvesting.

Particularly effective compounds are those of the formula I in which $R_1$ is hydrogen or $C_1$-$C_4$alkyl, $R_2$ is $C_1$-$C_6$alkyl or $C_1$-$C_4$alkoxy, $R_3$ is hydrogen, $C_1$-$C_4$alkyl, an alkali metal cation or an alkaline earth metal cation or a $C_1$-$C_4$alkylammonium group the alkyl moieties of which can be substituted by OH, CN or $C_1$-$C_4$alkoxy, each of $R_4$ and $R_5$ are hydrogen, each of $R_6$ and $R_7$ are hydrogen, $C_1$-$C_4$alkyl, or one of them is also phenyl, each of $R_8$ and $R_9$ is hydrogen, $C_1$-$C_4$alkyl, or one of them is also phenyl or a $C_1$-$C_4$alkoxycarbonyl radical, $X_1$ and $X_2$ together are a double bonded oxygen atom, and Y is oxygen or sulfur.

The best results are obtained with the compounds of formula I in which $R_1$ is hydrogen or $C_1$-$C_4$alkyl, $R_2$ is $C_1$-$C_6$alkyl or methoxy, $R_3$ is hydrogen or methyl, each of $R_4$ and $R_5$ is hydrogen, each of $R_6$ and $R_7$ is hydrogen or $C_1$-$C_4$alkyl, each of $R_8$ and $R_9$ is hydrogen or $C_1$-$C_4$alkyl, $X_1$ and $X_2$ together are a double bonded oxygen atom, and Y is oxygen.

In addition to containing the active ingredients of the formula I, the compositions of this invention contain a suitable carrier and/or other adjuvants. Suitable carriers and adjuvants can be solid or liquid and correspond to the substances customarily employed in the art of formulation, e.g. natural or regenerated mineral substances, solvents, diluents, dispersants, emulsifiers, wetting agents, tackifiers, thickeners, binders and/or fertilisers.

For use in herbicidal compositions, the compounds of the formula I can be processed to dusts, emulsifiable concentrates, granules, dispersions, or to solutions or suspensions in conventional formulation.

The benzthiazolylurea derivatives of the formula I are obtained by methods which are known per se, by reacting the appropriately substituted benzthiazolamine or benzthiazole isocyanate with a carbamoyl halide, an isocyanate or an amine.

One process for the production of the benzthiazolylurea derivatives of the formula I comprises reacting a benzthiazolamine of the formula II

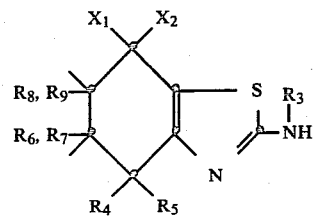

wherein $R_3$ and $R_9$ and $X_1$ and $X_2$ are as defined for formula I, in an inert solvent or diluent and in the presence of an acid acceptor, with a carbamoyl halide of the formula III

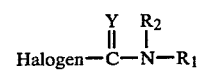

wherein $R_1$, $R_2$ and Y are as defined for formula I.

A process for the production of those benzthiazolylurea derivatives of the formula I, wherein $R_3$ is hydrogen, comprises reacting a benzthiazole isocyanate or isothiocyanate of the formula IV

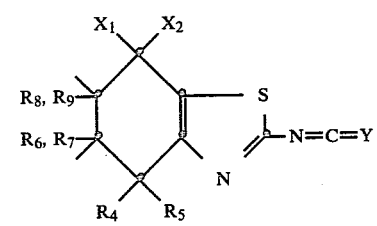

wherein $R_4$ to $R_9$ and $X_1$, $X_2$ and Y are as defined for formula I, in an inert solvent or diluent, with an amine of the formula V

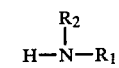

wherein $R_1$ and $R_2$ are as defined for formula I. If desired, the hydrogen atom $R_3$ can be replaced by an alkyl group with a suitable alkyl ester in the presence of a base, or by a basic salt radical with a strong base.

A process for the production of benzthiazolylurea derivatives of the formula I, wherein $R_2$ is hydrogen, comprises reacting a benzthiazolamine of the formula II, in an inert solvent or diluent, with an isocyanate or isothiocyanate of the formula VI

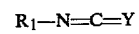

wherein $R_1$ and Y are as defined for formula I. If desired, the hydrogen atom $R_2$ can be replaced by an alkyl radical, in the presence of a base, with an appropriate alkyl ester.

These reactions are advantageously conducted in a protic organic solvent or diluent, e.g. an alcohol, an ester or ether, a ketone, dimethyl formamide, dimethyl sulfoxide or acetonitrile, alone or diluted with water.

The reaction temperatures are in the range from −10° to +150° C., but are conveniently in the range from room temperature to the boiling point of the mixture of solvents. The reaction time is from 1 hour to about a day, depending on the starting materials, the solvent and the temperature.

Where a halogen atom is split off during the reaction, the equimolar amount of an acid acceptor should be used. Suitable acid acceptors are, in principle, all inorganic or organic bases, e.g. NaOH, KOH, NaHCO$_3$, K$_2$CO$_3$ or potassium tert-butylate. However, it is preferred to use a secondary or tertiary amine such as trimethylamine, triethylamine, pyridine, 4-dimethylaminopyridine, potassium tert-butylate, and the like.

The starting benzthiazolamines of the formula II are obtained by reacting appropriately substituted cyclohexane-1,3-diones with thioureas, in an alkanolic solvent and in the presence of a small amount of iodine as catalyst, e.g. in accordance with the following reaction scheme:

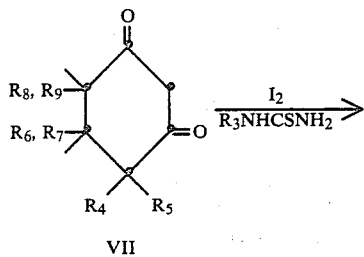

VII

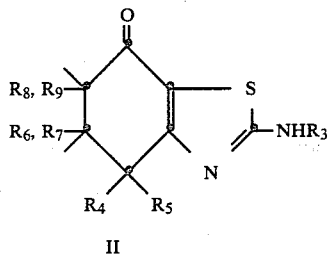

II

Further, the benzthiazolamines of the formula II can also be obtained by condensing aminonitrile, in the presence of sulfur, to a 3-oxo-4,5-dihydro-6H-aniline in accordance with the reaction scheme

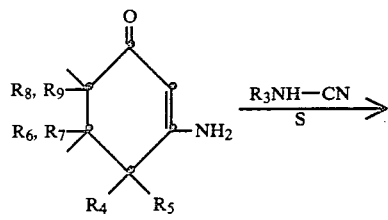

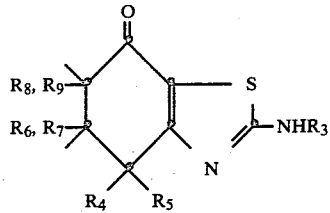

The diones of the formula VII and the anilines of the formula VIII can also be cyclised with an aminoisothiocyanate of the formula IX $$R_3NH-N=C=S \quad (IX)$$

In the above formulae, R$_1$ to R$_9$ are as defined for formula I. Such condensation reactions are to be found in Weissenberger, "The Chemistry of Heterocyclic Compounds," Vol. 34, Part 1, p. 213 ff., Part 2, p. 9 ff., and in Vol. 39, Part 1, p. 297 ff. (John Wiley+Sons, 1979). Particulars relating to the production of the starting materials or similar products are contained in German Offenlegungsschrift No. 1 932 699, U.S. Pat. Nos. 3,682,045 and 4,120,690, and in Swiss Pat. No. 528 533.

The compounds of the formula I are stable compounds which are soluble in customary organic solvents such as alcohols, ethers, ketones, dimethyl formamide, dimethyl sulfoxide etc. They are not explosive or corrosive, and no special precautionary measures are required for handling them.

The compositions of the present invention are obtained in known manner by intimately mixing and grinding active ingredients (compounds) of the general formula I with suitable carriers and/or adjuvants, with or without the addition of antifoams, wetting agents, dispersants and/or solvents which are inert to the active ingredients. The active ingredients can be processed to the following formulations:

solid formulations: dust, tracking powders, granules (coated granules, impregnated granules and homogeneous granules), active ingredient concentrates which are dispersible in water: wettable powders, pastes, emulsions, emulsifiable concentrates, liquid formulations: solutions, dispersions.

The concentrations of active ingredient in the compositions of this invention are between 1 and 80 percent by weight. As circumstances may require, the active ingredients can also be applied in low concentrations of about 0.05 to 1 percent by weight.

The compositions of the present invention can be mixed with other biocidal compounds or compositions. Thus in addition to containing the compounds of the formula I, the compositions of the invention can also contain e.g. insecticides, fungicides, bactericides, fungistatic agents, bacteriostatic agents, nematocides or further herbicides, in order to broaden the activity spectrum.

The following Examples describe in detail the production of a number of benzthiazolylurea derivatives of the formula I and compositions containing them. Further compounds obtained in similar manner are listed in the table following Example 5. Pressures are in millibars, and parts and percentages are by weight.

EXAMPLE 1

N-(5,5-Dimethyl-7-oxo-4,5-dihydro-6H-benzthiazol-2-yl)-N-methylurea

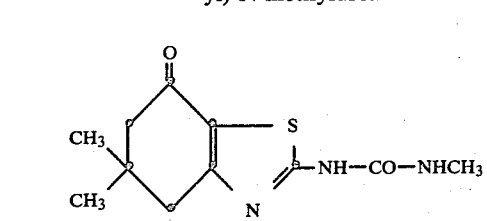

(a) 28 g of 2-bromo-5,5-dimethylcyclohexane-1,3-dione and 11.7 g of thiourea are dissolved in 200 ml of ethanol. After the weakly exothermic reaction has subsided, the mixture is refluxed for a further 6 hours. The solution is diluted with 400 ml of water and neutralised with saturated sodium bicarbonate solution. The precipitated crystals are collected by filtration and dried in vacuo at 80° C., affording 21 g of 2-amino-5,5-dimethyl-7-oxo-4,5-dihydro-6H-benzthiazole with a melting point of 203°-205° C.

(b) 9 g of the product obtained in (a) and 4 g of methyl isocyanate are dissolved in 150 ml of acetonitrile and the solution is stirred overnight at room temperature. The solution is then concentrated to one third of its volume and cooled to 0° C. The precipitated crystals are collected by filtration and dried in vacuo at 80° C., affording 11.5 g of the title compound in the form of colourless crystals with a melting point of 228°-231° C. (compound 1).

EXAMPLE 2

N-(5,5-Dimethyl-7-oxo-4,5-dihydro-6H-benzthiazol-2-yl)-N'-methyl-N'-methoxy-urea

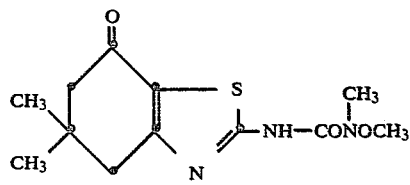

15 g of 2-amino-5,5-dimethyl-7-oxo-4,5-dihydro-6H-benzthiazole obtained in Example 1 (a) are dissolved in 100 ml of dimethyl formamide and to this solution are added 8.6 g of potassium tert-butylate. Then 11.3 g of methoxymethylcarbamoyl chloride are added dropwise at 0° C. and the reaction mixture is stirred for 3 hours at room temperature. The mixture is then poured into ice/water and extracted with chloroform. Chromatography on silica gel with chloroform/methanol (20:1) as eluant affords 8 g of the title compound with a melting point of 145°-148° C. (compound 3).

EXAMPLE 3

N-(5,5-Dimethyl-7-oxo-4,5-dihydro-6H-benzthiazol-2-yl)-N',N'-dimethylurea

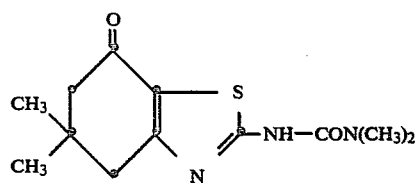

12 g of 2-amino-5,5-dimethyl-7-oxo-4,5-dihydro-6H-benzthiazole (Example 1 (a), 7.2 g of potassium tert-butylate and 8.6 g of dimethylcarbamoyl chloride are reacted as described in Example 2, affording 7.6 g of the title compound with a melting point of 175°-180° C. (compound 4).

EXAMPLE 4

N-Methyl-N-(5,5-dimethyl-7-oxo-4,5-dihydro-6H-benzthiazol-2-yl)-N'-methyl-urea

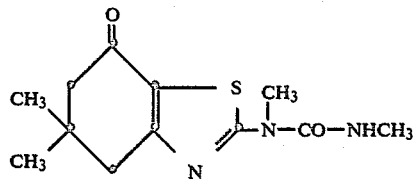

(a) 82 g of 2-bromo-5,5-dimethylcyclohexane-1,3-dione, 40 g of sodium acetate and 50 g of N-methylthiourea are dissolved in 500 ml of acetic acid. The mixture is stirred at room temperature until the weakly exothermic reaction has subsided, and then refluxed for 3 hours. The reaction mixture is then concentrated to one third of its volume in a rotary evaporator, poured into 100 ml of water and cooled to 0° C. The precipitate is collected by filtration and dried in vacuo at 80° C., affording 64 g of 2-methylamino-5,5-dimethyl-7-oxo-4,5-dihydro-6H-benzthiazole with a melting point of 217°-218° C.

(b) 15 g of the product obtained in (a) and 5 ml of methyl isocyanate are suspended in 100 ml of acetonitrile and stirred overnight at room temperature. 1 ml of triethylamine is added as catalyst (in a further experiment, 100 mg of 4-dimethylaminopyridine are added with equal success). The reaction solution is then concentrated in a rotary evaporator and the residue is crystallised from a mixture of chloroform/hexane (1:1), affording 14 g of the title compound with a melting point of 174°-175° C. (compound 4).

EXAMPLE 5

N-Methyl-N-(5,5-dimethyl-7-oxo-4,5-dihydro-6H-benzthiazol-2-yl)-N'-tert-butyl-urea

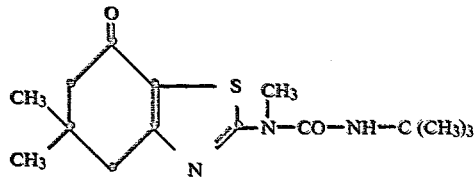

15 g of 2-methylamino-5,5-dimethyl-7-oxo-4,5-dihydro-6H-benzthiazole (obtained in Example 4 (a) are suspended in 100 ml of acetonitrile. Then 8.2 g of tert-butylisocyanate and 1 g of potassium tert-butylate are added at 0° C. The mixture is subsequently stirred for 24 hours at room temperature. Working up is as described in Example 4 (b), affording 10.8 g of the title compound in the form of colourless crystals with a melting point of 165°-167° C. (compound 5).

Further compounds which are obtained by procedures similar to those described in the foregoing Examples are listed in the following table:

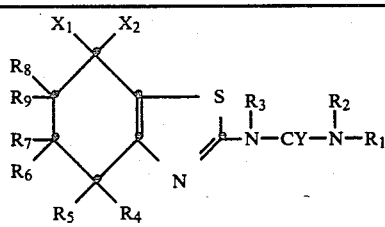

| NO. | R8, R9 | R6, R7 | R4, R5 | X1, X2 | Y | R3 | NR1R2 | physical data (°C.) |
|---|---|---|---|---|---|---|---|---|
| 1 | H2 | (CH3)2 | H2 | O | O | H | NHCH3 | m.p. 228-231° |
| 2 | H2 | (CH3)2 | H2 | O | O | CH3 | NHCH3 | m.p. 174-175° |
| 3 | H2 | (CH3)2 | H2 | O | O | H | N(CH3)OCH3 | m.p. 145-8° |
| 4 | H2 | (CH3)2 | H2 | O | O | H | N(CH3)2 | m.p. 175-180° |
| 5 | H2 | (CH3)2 | H2 | O | O | CH3 | N(CH3)OCH3 | m.p. 108-110° |
| 6 | H2 | (CH3)2 | H2 | O | O | H | NHC4H9n | m.p. 204-6° |
| 7 | H2 | (CH3)2 | H2 | O | O | CH3 | NHC4H9n | m.p. 124-6° |
| 8 | H2 | (CH3)2 | H2 | O | O | CH3 | NHC4H9 tert | m.p. 165-7° |
| 9 | H2 | (CH3)2 | H2 | O | O | CH3 | N(CH3)2 | m.p. 165-7° |
| 10 | H2 | (CH3)2 | H2 | O | O | Na | N(CH3)2 | |
| 11 | H2 | (CH3)2 | H2 | O | O | Na | N(CH3) OCH3 | |
| 12 | H2 | (CH3)2 | H2 | O | S | CH3 | NHCH3 | m.p. 157-60° |
| 13 | H2 | (CH3)2 | H2 | O | O | NH3C3H7 iso | N(CH3)OCH3 | |
| 14 | H2 | (CH3)2 | H2 | O | O | NH3C3H7 iso | N(CH3) OCH3 | |
| 15 | H2 | (CH3)2 | H2 | O | O | NH(CH3)3 | N(CH3)OCH3 | |
| 16 | H2 | (CH3)2 | H2 | O | O | H | 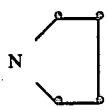 | |
| 17 | H2 | (CH3)2 | H2 | O | O | NH(CH3)3 | N(CH3)2 | |
| 18 | H2 | (CH3)2 | H2 | O | O | H | 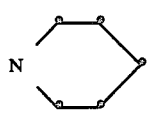 | |
| 19 | H2 | (CH3)2 | H2 | O | O | H | 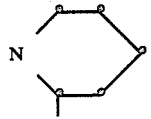 | |
| 20 | H2 | (CH3)2 | H, COOCH3 | O | O | CH3 | NHCH3 | |
| 21 | H2 | (CH3)2 | H, COOCH3 | O | O | CH3 | NHC4H9 n | |
| 22 | H2 | (CH3)2 | H, COOCH3 | O | O | H | N(CH3)2 | |
| 23 | H2 | (CH3)2 | H, COOCH3 | O | O | H | N(CH3)OCH3 | |
| 24 | H2 | (CH3)2 | H, COOCH3 | O | S | CH3 | NHCH3 | |
| 25 | H2 | (CH3)2 | H, CN | O | O | CH3 | NHCH3 | |
| 26 | H2 | (CH3)2 | H, CN | O | O | CH3 | N(CH3)OCH3 | |
| 27 | H2 | (CH3)2 | H, CN | O | O | H | N(CH3)2 | |
| 28 | H2 | (CH3)2 | H,  | O | O | CH3 | NHCH3 | |
| 29 | H2 | (CH3)2 | H,  | O | O | H | N(CH3)2 | |
| 30 | H2 | (CH3)2 | H,  | O | O | H | N(CH3)OCH3 | |
| 31 | H2 | (CH3)2 | CH3, COOCH3 | O | O | CH3 | NHCH3 | |
| 32 | H2 | (CH3)2 | CH3, COOCH3 | O | O | CH3 | NHC4H9 n | |
| 33 | H2 | (CH3)2 | CH3, COOCH3 | O | O | H | N(CH3)2 | |
| 34 | H2 | (CH3)2 | CH3, COOCH3 | O | O | H | N(CH3)OCH3 | |
| 35 | H2 | (CH3)2 | CH3, COOH | O | O | CH3 | NHCH3 | |
| 36 | H2 | (CH3)2 | CH3, COOH | O | O | H | N(CH3)2 | |
| 37 | H2 | (CH3)2 | CH3, COOH | O | O | H | N(CH3)OCH3 | |
| 38 | H2 | (CH3)2 | H, Br | O | O | H | N(CH3)2 | |
| 39 | H2 | (CH3)2 | H, Br | O | O | CH3 | NHCH3 | |

-continued

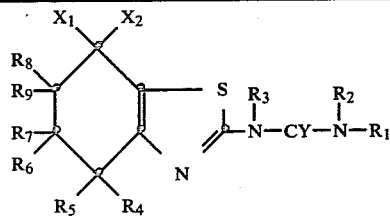

| NO. | R8, R9 | R6, R7 | R4, R5 | X1, X2 | Y | R3 | NR1R2 | physical data (°C.) |
|---|---|---|---|---|---|---|---|---|
| 40 | H2 | (CH3)2 | H, Br | O | O | H | N(CH3)OCH3 | |
| 41 | H2 | (CH3)2 | H, COOCH3 | O | O | Na | N(CH3)2 | |
| 42 | H2 | (CH3)2 | H, COOCH3 | O | O | Na | N(CH3)OCH3 | |
| 43 | H2 | (CH3)2 | H, COOCH3 | O | O | NH3C3H7 iso | N(CH3)2 | |
| 44 | H2 | (CH3)2 | H, COOCH3 | O | O | NH3C3H7 iso | N(CH3)OCH3 | |
| 45 | H2 | (CH3)2 | H, COOCH3 | O | O | NH(CH3)3 | N(CH3)2 | |
| 46 | H2 | (CH3)2 | H, COOCH3 | O | O | NH(CH3)3 | N(CH3)OCH3 | |
| 47 | H2 | (CH3)2 | H, COOCH3 | O | O | H | N-azetidinyl | |
| 48 | H2 | (CH3)2 | H, COOCH3 | O | O | H | N-piperidinyl | |
| 49 | H2 | (CH3)2 | H, COOCH3 | O | O | H | N-(4-methylpiperidinyl) | |
| 50 | H2 | (CH3)2 | H, CONH2 | O | O | H | N(CH3)2 | |
| 51 | H2 | (CH3)2 | H, CONHC2H5 | O | O | H | N(CH3)2 | |
| 52 | H2 | (CH3)2 | H, COOC4H9n | O | O | H | N(CH3)2 | |
| 53 | H, COOCH3 | (CH3)2 | H2 | O | O | CH3 | NHCH3 | m.p. 152–154° |
| 54 | H, COOCH3 | (CH3)2 | H2 | O | O | CH3 | NHC4H9n | |
| 55 | H, COOCH3 | (CH3)2 | H2 | O | O | H | N(CH3)2 | |
| 56 | H, COOCH3 | (CH3)2 | H2 | O | O | H | N(CH3)OCH3 | m.p. 80–88° |
| 57 | H, COOCH3 | (CH3)2 | H2 | O | S | CH3 | NHCH3 | |
| 58 | H, CH3 | (CH3)2 | H2 | O | O | CH3 | NHCH3 | m.p. 133–136° |
| 59 | H, CN | (CH3)2 | H2 | O | O | H | N(CH3)2 | |
| 60 | H, CH3 | (CH3)2 | H2 | O | O | CH3 | N(CH3)OCH3 | m.p. 111–118° |
| 61 | H, (fused ring) | (CH3)2 | H2 | O | O | CH3 | NHCH3 | |
| 62 | H, (fused ring) | (CH3)2 | H2 | O | O | H | N(CH3)2 | |
| 63 | H, (fused ring) | (CH3)2 | H2 | O | O | H | N(CH3)2OCH3 | |
| 64 | CH3, COOCH3 | (CH3)2 | H2 | O | O | CH3 | NHCH3 | m.p. 178–179° |
| 65 | CH3, COOCH3 | (CH3)2 | H2 | O | O | CH3 | NHC4H9N | |
| 66 | CH3, COOCH3 | (CH3)2 | H2 | O | O | H | N(CH3)2 | |
| 67 | CH3, COOCH3 | (CH3)2 | H2 | O | O | H | N(CH3)OCH3 | m.p. 100–104° |
| 68 | CH3, COOH | (CH3)2 | H2 | O | O | CH3 | NHCH3 | |
| 69 | CH3, COOH | (CH3)2 | H2 | O | O | H | N(CH3)2 | |
| 70 | CH3, COOH | (CH3)2 | H2 | O | O | H | N(CH3)OCH3 | |
| 71 | Br, H | (CH3)2 | H2 | O | O | H | N(CH3)2 | |
| 72 | Br, H | (CH3)2 | H2 | O | O | CH3 | NHCH3 | |
| 73 | Br, H | (CH3)2 | H2 | O | O | H | N(CH3)OCH3 | |
| 74 | H, COOCH3 | (CH3)2 | H2 | O | O | Na | N(CH3)2 | |
| 75 | H, COOCH3 | (CH3)2 | H2 | O | O | Na | N(CH3)OCH3 | |
| 76 | H, COOCH3 | (CH3)2 | H2 | O | O | NH3C3H7 iso | N(CH3)2 | |
| 77 | H, COOCH3 | (CH3)2 | H2 | O | O | NH3C3H7 iso | N(CH3)OCH3 | |
| 78 | H, COOCH3 | (CH3)2 | H2 | O | O | NH(CH3)3 | N(CH3)2 | |
| 79 | H2 | C3H7iso, H | H2 | O | O | CH3 | N(CH3)OCH3 | m.p. 106–107° |

-continued

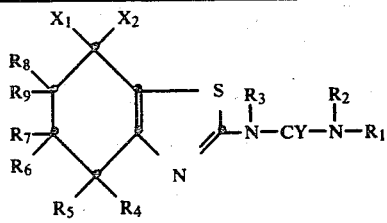

| NO. | R8, R9 | R6, R7 | R4, R5 | X1, X2 | Y | R3 | NR1R2 | physical data (°C.) |
|---|---|---|---|---|---|---|---|---|
| 80 | H, COOCH3 | (CH3)2 | H2 | O | O | H | (azetidine ring, N) | |
| 81 | H2COOCH3 | (CH3)2 | H2 | O | O | H | (piperidine ring, N) | |
| 82 | H, COOCH3 | (CH3)2 | H2 | O | O | H | (methylpiperidine, N, CH3) | |
| 83 | H | C4H9(t), H | H2 | O | O | CH3 | NHC4H9n | m.p. 125–129° |
| 84 | H, CH3 | (CH3)2 | H2 | O | O | CH3 | NHC4H9n | m.p. 92–95° |
| 85 | H2 | (CH3)2 | H2 | O | O | CH3 | NHC2H5 | m.p. 144–145° |
| 86 | H2 | H2 | H2 | O | O | H | N(CH3)2 | m.p. 178–181° |
| 87 | H2 | H2 | H2 | O | O | H | NHCH3 | m.p. 225–228° |
| 88 | H2 | H2 | H2 | O | O | H | N(CH3)OCH3 | m.p. 165–167° |
| 89 | H2 | H2 | H2 | O | O | CH3 | NHCH3 | |
| 90 | H2 | H2 | (ring, H, CF3) | O | O | H | N(CH3)2 | |
| 91 | H2 | H2 | (ring, H) | O | O | H | N(CH3)OCH3 | |
| 92 | H2 | | (ring, H) | O | O | CH3 | NHCH3 | |
| 93 | (ring, H, CF3) | H2 | H2 | O | O | H | N(CH3)2 | |
| 94 | (ring, H) | H2 | H2 | O | O | H | N(CH3)OCH3 | |
| 95 | (ring, H) | H2 | H2 | O | O | CH3 | NHCH3 | |
| 96 | H2 | (ring, H, CF3) | H2 | O | O | H | N(CH3)2 | |
| 97 | H2 | (ring, H) | H2 | O | O | H | N(CH3)OCH3 | |
| 98 | H2 | (ring, H) | H2 | O | O | CH3 | NHCH3 | m.p. 170–175° |

-continued

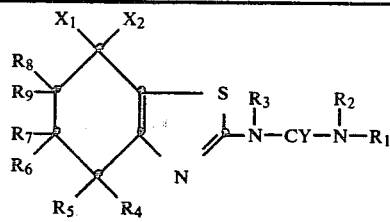

| NO. | R8, R9 | R6, R7 | R4, R5 | X1, X2 | Y | R3 | NR1R2 | physical data (°C.) |
|---|---|---|---|---|---|---|---|---|
| 99 | H2 | H, ⌬-Cl | H, COOCH3 | O | O | H | N(CH3)2 | |
| 100 | H2 | H, ⌬ | H, COOCH3 | O | O | H | N(CH3)OCH3 | |
| 101 | H2 | H, ⌬-CF3 | H, COOCH3 | O | O | CH3 | NHCH3 | |
| 102 | H, COOCH3 | H, ⌬ | H2 | O | O | H | N(CH3)2 | m.p. 140–150° |
| 103 | H, COOCH3 | H, ⌬ | H2 | O | O | H | N(CH3)OCH3 | m.p. 80° |
| 104 | H, COOCH3 | H, ⌬ | H2 | O | O | CH3 | NHCH3 | m.p. 173–175° C. |
| 105 | H2 | H, C3H7 iso | H2 | O | O | H | N(CH3)2 | |
| 106 | H2 | H, C3H7 iso | H2 | O | O | H | N(CH3)OCH3 | |
| 107 | H2 | H, C3H7 iso | H2 | O | O | CH3 | NHCH3 | m.p. 134–136° |
| 108 | H2 | H, C3H7 iso | H, COOCH3 | O | O | H | N(CH3)2 | |
| 109 | H2 | H, C3H7 iso | H, COOCH3 | O | O | H | N(CH3)OCH3 | |
| 110 | H2 | H, C3H7 iso | H, COOCH3 | O | O | CH3 | NHCH3 | |
| 111 | H, COOCH3 | H, C3H7 iso | H2 | O | O | H | N(CH3)2 | |
| 112 | H, COOCH3 | H, C3H7 iso | H2 | O | O | H | N(CH3)OCH3 | m.p. 185–190° |
| 113 | H, COOCH3 | H, C3H7 iso | H2 | O | O | CH3 | NHCH3 | m.p. 130–135° |
| 114 | H2 | H, C4H9t | H2 | O | O | H | N(CH3)2 | |
| 115 | H2 | H, C4H9t | H2 | O | O | H | N(CH3)OCH3 | m.p. 95° |
| 116 | H2 | H, C4H9t | H2 | O | O | CH3 | NHCH3 | m.p. 150–152° |
| 117 | H2 | H, C4H9t | H, COOCH3 | O | O | H | N(CH3)2 | |
| 118 | H2 | H, C4H9t | H, COOCH3 | O | O | H | N(CH3OCH3 | |
| 119 | H2 | H, C4H9t | H, COOCH3 | O | O | CH3 | NHCH3 | |
| 120 | H, COOCH3 | H, C4H9t | H2 | O | O | H | N(CH3)2 | |
| 121 | H, COOCH3 | H, C4H9t | H2 | O | O | H | N(CH3)OCH3 | |
| 122 | H, COOCH3 | H, C4H9t | H2 | O | O | CH3 | NHCH3 | |
| 123 | H2 | H, C=CH ⌬ | H2 | O | O | CH3 | NHCH3 | |
| 124 | H2 | H, ⌬ | H, ⌬ | O | O | H | N(CH3)2 | |
| 125 | H2 | H, CH=CH—CH3 | H2 | O | O | CH3 | NHCH3 | |
| 126 | H2 | H, CH2CH(CH3)<br>S—C2H5 | H2 | O | O | CH3 | NHCH3 | |
| 127 | H, ⌬ | H, ⌬ | H2 | O | O | CH3 | NHCH3 | |
| 128 | H, (CH2)4 H | | H2 | O | O | CH3 | NHCH3 | |
| 129 | H (CH2)4 H | | H2 | O | O | CH3 | NHCH3 | |
| 130 | H2 | (CH3)2 | H2 | O(CH2)2O | O | CH3 | NHCH3 | |
| 131 | H2 | (CH3)2 | H2 | S(CH2)2S | O | CH3 | NHCH3 | |
| 132 | H2 | (CH3)2 | H2 | O(CH2)2O | O | H | N(CH3)2 | |
| 133 | H2 | (CH3)2 | H, COOCH3 | O(CH2)2O | O | H | N(CH3)2 | |

-continued

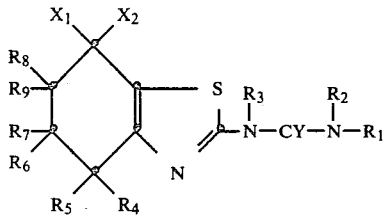

| NO. | R8, R9 | R6, R7 | R4, R5 | X1, X2 | Y | R3 | NR1R2 | physical data (°C.) |
|---|---|---|---|---|---|---|---|---|
| 134 | H2 | H2 | H2 | O(CH2)2O | O | CH3 | NHCH3 | |
| 135 | H, COOCH3 | (CH3)2 | H2 | O(CH2)2O | O | CH3 | NHCH3 | |
| 136 | H2 | H, C3H7 iso | CH3 COOCH3 | O(CH2)2O | O | H | N(CH3)OCH3 | |
| 137 | H, CH3 | H, C3H7 (i) | H | O | O | CH3 | N(CH3)2 | |
| 138 | H, CH3 | H, C3H7(i) | H2 | O | O | CH3 | NHCH3 | |
| 139 | H, C2H5 | H, C3H7(i) | H2 | O | O | CH3 | NHC4H9(n) | |
| 140 | H, C2H5 | (CH3)2 | H2 | O | O | CH3 | N(CH3)2 | |
| 141 | H C2H5 | (CH3)2 | H2 | O | O | CH3 | NHCH3 | |
| 142 | H C2H5 | C3H7(i), H | H2 | O | O | H | N(CH3)OCH3 | |
| 143 | H C3H7n | (CH3)2 | H2 | O | O | CH3 | NHCH3 | |
| 144 | H C3H7n | (CH3)2 | H2 | O | O | H | N(CH3)2 | |
| 145 | H C4H9n | (CH3)2 | H2 | O | O | CH3 | NHCH3 | |
| 146 | H C4H9n | (CH3)2 | H2 | O | O | H | N(CH3)OCH3 | |

EXAMPLE 6

The compounds of formula I can be formulated to herbicidal compositions e.g. by one of the following procedures.

Granules

The following substances are used to formulate 5% granules:
- 5 parts of N-(5,5-dimethyl-7-oxo-4,5-dihydro-6H-benzthiazol-2-yl)-N'-methyl-urea,
- 0.25 part of epichlorohydrin,
- 0.25 part of cetyl polyglycol ether,
- 3.50 parts of polyethylene glycol,
- 91 parts of kaolin (particle size 0.3–0.8 mm).

The active ingredient is mixed with epichlorohydrin and the mixture is dissolved in 6 parts of acetone; the polyethylene glycol and cetyl polyglycol ether are then added. The resultant solution is sprayed on kaolin, and the acetone is subsequently evaporated in vacuo.

Wettable Powder

The following constituents are used to formulate (a) a 70% and (b) a 10% wettable powder:

(a)
- 70 parts of N-(5,5-dimethyl-7-oxo-4,5-dihydro-6H-benzthiazol-2-yl)-N'-methyl-N'-methoxy-urea,
- 5 parts of sodium dibutylnaphthylsulfonate,
- 3 parts of naphthalenesulfonic acid/phenolsulfonic acid/formaldehyde condensate (3:2:1),
- 10 parts of kaolin,
- 12 parts of Champagne chalk;

(b)
- 10 parts of the above compound,
- 3 parts of a mixture of the sodium salts of saturated fatty alcohol sulfates,
- 5 parts of naphthalenesulfonic acid/formaldehyde condensate,
- 83 parts of kaolin.

The active ingredient is applied to the corresponding carriers (kaolin and chalk) and then these are mixed and ground, to yield wettable powders of excellent wettability and suspension power. By diluting these wettable powders with water it is possible to obtain suspensions containing 0.1 to 8% of active ingredient. These suspensions are suitable for controlling weeds in cultivations of plants.

Paste

The following substances are used to formulate a 45% paste:
- 45 parts of N-(5,5-dimethyl-7-oxo-4,5-dihydro-6H-benzthiazol-2-yl)-N',N'-dimethylurea,
- 5 parts of sodium aluminum silicate,
- 14 parts of cetyl polyglycol ether with 8 moles of ethylene oxide,
- 1 part of oleyl polyglycol ether with 5 moles of ethylene oxide,
- 2 parts of spindle oil,
- 10 parts of polyethylene glycol,
- 23 parts of water.

The active ingredient is intimately mixed with the adjuvants in appropriate devices and ground. By diluting the resultant paste with water, it is possible to prepare suspensions of the desired concentration.

Emulsifiable Concentrate

The following ingredients are mixed to formulate a 25% emulsifiable concentrate:
- 25 parts of N-methyl-N-(5,5-dimethyl-7-oxo-4,5-dihydro-6H-benzthiazol-2-yl)-N'-methylurea,
- 5 parts of a mixture of nonylphenolpolyoxyethylene and calcium dodecylbenzenesulfonate,
- 15 parts of cyclohexanone,
- 55 parts of xylene.

This concentrate can be diluted with water to give emulsions in suitable concentrations.

EXAMPLE 7

The following test methods were employed to determine the herbicidal and plant growth-inhibiting action of the compounds of formula I.

Preemergence herbicidal action

In a greenhouse, plant seeds are sown in flower pots of 12–15 cm in diameter such that 12–25 plants are able to develop in each pot. Directly after sowing, the surface of the soil is treated with an aqueous suspension of the active ingredients, obtained from a 10% wettable powder. Four different concentration series are employed, corresponding to rates of application of 4, 2, 1 and 0.5 kg of active ingredient per hectare respectively. The pots are then kept in the greenhouse at 22°–25° C. and 50–70% relative humidity. The test is evaluated after 3 weeks and the state of the plants is assessed in accordance with the following rating:
- 9 = normal growth, as untreated controls
- 8–2 = increasing stages of damage
- 1 = plant withered The results are reported in the following table.

|  | Compound | | | | |
|---|---|---|---|---|---|
|  | 2 | 3 | 4 | 9 | 58 |
|  | Rate of application in kg/ha: | | | | |
| Plants: | 4 2 | 4 2 | 4 2 | 4 2 | 4 2 |
| *Avena fatua* | 1 1 | 1 2 | 1 1 | 1 1 | 1 1 |
| *Bromus tectorum* | 1 1 | 2 3 | 1 2 | 1 1 | 1 1 |
| *Lolium perenne* | 1 1 | 2 2 | 2 3 | 1 1 | 1 2 |
| *Alopecurus myos.* | 1 1 | 2 2 | 2 2 | 1 1 | 1 1 |
| *Sorghum halepense* | 1 1 | 1 1 | 1 1 | 1 1 | 1 2 |
| Abutilon | 1 1 | 1 1 | 1 1 | 1 1 | 1 1 |
| *Sida spinosa* | 1 1 | 1 1 | 1 2 | 1 1 | 1 1 |
| *Amaranthus retrofl.* | 1 1 | 1 1 | 1 1 | 1 1 | 1 1 |
| *Solanum nirgrum* | 1 1 | 1 1 | 1 1 | 1 1 | 1 1 |
| *Ipomoea purpurea* | 1 1 | 1 1 | 1 1 | 1 1 | 1 1 |
| *Sinapis alba* | 1 1 | 1 1 | 1 1 | 1 1 | 1 1 |
| *Stellaria media* | 1 1 | 1 1 | 1 1 | 1 1 | 1 1 |
| *Chrysanthemum leuc.* | 1 1 | 1 1 | 1 1 | 1 1 | 1 1 |

Postemergence herbicidal action

Different cultivated plants and weeds are reared from seeds in pots in a greenhouse until they have reached the 4–6 leaf stage. The plants are then sprayed with aqueous emulsions (obtained from a 5% emulsifiable concentrate) at different rates of application. The treated plants are then kept under optimum conditions of light, regular watering, 22°–25° C. and 50–70% relative humidity. The test is evaluated 15 days after treatment. The state of the plants is assessed in accordance with the same rating as employed for the preemergence test, and the results are reported in the following table.

|  | Compound | | | | | |
|---|---|---|---|---|---|---|
|  | 2 | 3 | 4 | 5 | 9 | 58 |
|  | Rate of application in kg/ha: | | | | | |
| Plants: | 4 2 | 4 2 | 4 2 | 4 2 | 4 2 | 4 2 |
| *Avena fatua* | 1 1 | 1 2 | 2 2 | 1 2 | 1 1 | 1 2 |
| *Lolium perenne* | 1 1 | 1 2 | 4 7 | 2 2 | 1 1 | 1 4 |
| *Alopecurus myos uroides* | 1 1 | 1 2 | 2 2 | 2 3 | 1 1 | 1 2 |
| *Digitaria sangiunalis* | 1 1 | 2 2 | 1 1 | 1 2 | 1 1 | 3 4 |
| *Echinochloa crus galli* | 1 1 | 2 3 | 2 2 | 2 4 | 1 2 | 1 2 |
| Abutilon | 1 1 | 1 1 | 1 1 | 1 1 | 1 1 | 1 1 |
| *Sida spinosa* | 1 1 | 1 1 | 1 1 | 1 1 | 1 1 | 1 1 |
| *Amaranthus retrofl.* | 1 1 | 1 1 | 1 1 | 1 1 | 1 1 | 1 1 |
| *Solanum nigrum* | 1 1 | 1 1 | 1 1 | 1 1 | 1 1 | 1 1 |
| *Ipomea purpurea* | 1 1 | 1 1 | 1 1 | 1 1 | 1 1 | 1 1 |
| *Sinapis alba* | 1 1 | 1 1 | 1 1 | 1 1 | 1 1 | 1 1 |
| *Stellaria media* | 1 1 | 1 1 | 1 1 | 1 1 | 1 1 | 1 1 |
| *Chrysanthemum leuc.* | 1 1 | 1 1 | 1 1 | 1 1 | 1 1 | 1 1 |
| *Galium aparine* | 1 1 | 1 1 | 1 1 | 1 1 | 1 1 | 1 1 |
| *Sesbania exaltata* | 1 1 | 1 1 | 1 1 | 1 1 | 1 1 | 1 1 |

Growth regulation and yield increase in soybeans

Soybeans of the "Hark" variety are sown in plastic containers in an earth/turf/sand mixture (6:3:1) in a climatic chamber in a greenhouse. By means of an optimum control of temperature, watering and lighting, as well as by addition of fertiliser, plants in the 5–6 trefoil leaf stage were able to develop after about 5 weeks. At this time the plants are sprayed with aqueous mixtures of an active ingredient in concentrations of 10, 50, 100 and 500 ppm until they are dripping wet. The plants are then further reared until the test is evaluated 5 weeks after treatment. Compared with untreated controls, 10 soybean plants treated with compound 83 at rates of application of 50 and 100 ppm exhibited the following features:
- a respective increase in weight of the harvested siliques of 13 and 17%,
- a reduction of the growth in height of 9 and 14% respectively,
- an average growth of sucker formation of 5–11%.

Desiccation and defoliation action

Cotton plants of the variety Deltapine are reared in earthenware pots in a greenhouse. After the first capsules have formed, the plants are sprayed with aqueous compositions of compound 1 at a rate of application corresponding to 1, 2, 0.6 and 0.3 kg/ha respectively in field application. Untreated plants act as controls. Evaluation of the test is made 3, 7 and 14 days after application of the active ingredient by determining the degree of defoliation (percentage of fallen leaves) and of desiccation (drying out of the leaves remaining on the plant). Plants treated with compounds 9, 58, 60 and 86 at rates of application of 1.2 and 0.6 kg/ha are left after 2 weeks with only a few dried out leaves.

What is claimed is:

1. A benzthiazolylurea of the formula

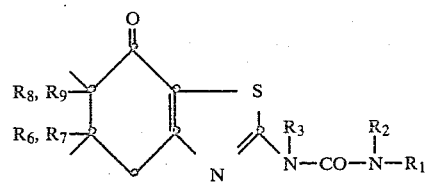

wherein
$R_1$ is hydrogen or $C_1$–$C_4$ alkyl,
$R_2$ is $C_1$–$C_6$ alkyl or methoxy,
or
$R_1$ and $R_2$ together with the nitrogen atom to which they are attached form a piperidino or pyrrolidino group which can be substituted by $C_1$–$C_3$ alkyl, and each of $R_6$, $R_7$, $R_8$ and $R_9$ is hydrogen or non-sterically hindering $C_1$–$C_4$ alkyl.

2. A benzthiazolylurea according to claim 1 wherein $R_1$ is hydrogen or $C_1$–$C_4$ alkyl, and $R_2$ is $C_1$–$C_6$ alkyl or methoxy.

3. N-Methyl-N-(5,5-dimethyl-7-oxo-4,5-dihydro-6H-benzthiazol-2-yl)-N',N'-dimethylurea, according to claim 2.

4. N-Methyl-N-(5,5-dimethyl-7-oxo-4,5-dihydro-6H-benzthiazol-2-yl)-N'-methyl-N'-methoxy-urea, according to claim 2.

5. N-Methyl-N-(5,5-dimethyl-7-oxo-4,5-dihydro-6H-benzthiazol-2-yl)-N',N'-dimethylurea, according to claim 2.

6. N-Methyl-N-(5,5-dimethyl-7-oxo-4,5-dihydro-6H-benzthiazol-2-yl)-N'-methyl-N'-methoxy-urea, according to claim 2.

7. N-Methyl-N-(5,5-dimethyl-7-oxo-4,5-dihydro-6H-benzthiazol-2-yl)-N'-methylurea, according to claim 2.

8. N-Methyl-N-(5,5,6-trimethyl-7-oxo-4,5-dihydro-6H-benzthiazol-2-yl)-N'-methylurea, according to claim 2.

9. N-Methyl-N-(5-tert-butyl-7-oxo-4,5-dihydro-6H-benzthiazol-2-yl)-N'-n-butyl-urea, according to claim 2.

10. N-Methyl-N-(5,5,6-trimethyl-7-oxo-4,5-dihydro-6H-benzthiazol-2-yl)-N'-methyl-N'-methoxy-urea, according to claim 2.

UNITED STATES PATENT AND TRADEMARK OFFICE
CERTIFICATE OF CORRECTION

PATENT NO. : 4,380,640

DATED : April 19, 1983

INVENTOR(S) : Hans George Brunner

It is certified that error appears in the above-identified patent and that said Letters Patent are hereby corrected as shown below:

Column 20, insert after line 38:

-- $R_3$ is hydrogen or methyl --

Signed and Sealed this

Sixth Day of December 1983

[SEAL]

Attest:

GERALD J. MOSSINGHOFF

Attesting Officer   Commissioner of Patents and Trademarks